United States Patent [19]

Suresh et al.

[11] Patent Number: 5,066,809

[45] Date of Patent: Nov. 19, 1991

[54] PREPARATION OF 3-METHYLPYRIDINE FROM 2-METHYLGLUTARONITRILE

[75] Inventors: Dev D. Suresh, Hudson, Ohio; Robert DiCosimo, Wilmington, Del.; Richard Loiseau, Bainbridge, Ohio; Maria S. Friedrich, Lyndhurst, Ohio; Hsiao-Chiung Szabo, Mentor, Ohio

[73] Assignee: The Standard Oil Company, Cleveland, Ohio

[21] Appl. No.: 589,307

[22] Filed: Sep. 27, 1990

[51] Int. Cl.$^5$ ............................................ C07D 213/08
[52] U.S. Cl. ...................................... 546/250; 546/251
[58] Field of Search ................................ 546/250, 251

[56] References Cited

U.S. PATENT DOCUMENTS 4,521,602  6/1985  Rebafka et al. .................... 546/184

OTHER PUBLICATIONS

Chemical Abstracts, vol. 98, No. 11, Abstract 89185h, pp. 541–542, Quarroz, Mar. 14, 1983.

*Primary Examiner*—C. Warren Ivy
*Assistant Examiner*—Zinna Northington-Davis
*Attorney, Agent, or Firm*—C. S. Lynch; M. F. Esposito; L. W. Evans

[57] ABSTRACT

Disclosed is a process for making 3-methylpyridine by contacting 2-methylglutaronitrile in admixture with hydrogen gas with a supported solid catalyst containing palladium metal promoted with at least one of Cr, W, Ni, Co and Ge.

7 Claims, No Drawings

PREPARATION OF 3-METHYLPYRIDINE FROM 2-METHYLGLUTARONITRILE

This invention concerns the catalytic conversion of 2-methylglutaronitrile to 3-methylpyridine by contacting the glutaronitrile in admixture with hydrogen gas over a solid catalyst comprising supported palladium metal promoted with at least one of W, Cr, Ni, Co and Ge.

In Lonza European Patent Application No. 82-102,584.8, 2-methylglutaronitrile containing ethyl succinonitrile was passed over Pd on alumina catalyst while admixed with $H_2$. The main product was amino-3-picolines but some 3-methylpyridine was also reported.

In BASF European Patent Application No. 82-100,681.4 there is disclosed the reaction of a mixture of 2-methylglutaronitrile and hydrogen by passing the mixture over a Pd catalyst supported on alumina.

It will thus be seen that supported palladium catalysts are old in the art for this reaction.

It is an object of the present invention to provide an improved catalytic process for making 3-methylpyridine from 2-methylglutaronitrile and $H_2$. It is another object of the invention to provide an improved supported palladium catalyst for such process.

Other objects, as well as aspects, features and advantages of the present invention will become apparent from a study of this specification, including the examples, and the claims.

These and other objects are realized by the present invention in accordance with which there is provided a process for making 3-methylpyridine by contacting 2-methylglutaronitrile (MGN) in admixture with hydrogen gas with a supported solid catalyst containing palladium metal promoted with at least one of Cr, W, Ni, Co and Ge. The MGN is usually in the vapor phase. The support is usually an essentially inert inorganic oxide. Usual supports are alumina-containing supports containing zero to 50 weight percent silica and 100 to 50 weight percent alumina. Now preferred supports contain zero to 30 weight percent silica and 100 to 70 weight percent alumina, with about 90% alumina/10% silica giving very superior results for these promoted catalysts in this particular reaction.

According to the present invention, the process of catalytically reacting 2-methylglutaronitrile in admixture with hydrogen gas in the vapor phase is improved by using the foregoing promoted catalysts in place of the prior art palladium catalysts.

The reaction can be effected in fixed bed reactors, fluidized bed or transport reactors, gravity flow moving bed reactors or any other conventional mode for reactions using solid catalysts.

Although details of reaction conditions are not part of the invention, usual reaction temperatures are about 250° to 320° C., reaction zone pressures are usually near atmospheric, although higher or lower pressures can be used, and contact times are usually 0.1 to 20 seconds. The molar ratio of $H_2$ to 2-methylglutaronitrile is generally about 2-100, although we usually recommend a ratio of about 10 to 60.

The ratio of the Pd metal to the support is not critical, but no more than 10 g per 100 g of support is usual for economic reasons, usually no more than 5 g, and most generally no more than 3 g per 100 g of support. As little as 0.1 g of Pd per 100 g of support, or even lower, can be used, but usually at least 0.2 g of Pd metal per 100 g of support is used. The promoters, singly or as a group, are present in amounts of up to 20 g per 100 g of support, and usually at least 0.05 g per 100 g of support the amounts being expressed as the free metals, even though promoters may be present as oxides.

The following examples are illustrative and are not to be considered limiting in any way. In the examples describing making the catalysts, the final step is omitted, but in every case this final step was the reduction of the Pd compound to Pd metal by treatment with hydrogen for one hour at 280° C. It should be noted that the promoters are expressed in weight percent of the metal even though they may be present as oxides. The hydrogen pretreatment reduces the Pd compound to the metal, but the promoters may or may not be reduced to metal by the pretreatment, or by the atmosphere prevailing during the MGN conversion reaction.

CATALYST EXAMPLE 1

A catalyst, 1.0 wt % Pd and 0.1 wt % W on 50% $Al_2O_3$/50% $SiO_2$, was made as follows:

SUPPORT: 238.1 g of alumina sol (21% $Al_2O_3$) were combined with 125.0 g of silica sol (40% $SiO_2$). The mixture gelled immediately. It was mixed thoroughly by hand, was dried at 120° C., heat treated at 290° C. for 3 hours and at 425° C. for 3 hours, then ground to 20-35 mesh size.

CATALYST: 5.00 g of above support were impregnated with a solution consisting of a mixture of 0.0833 g of $PdCl_2$ dissolved in 1N HCl, and of 0.0074 g of ammonium-meta-tungstate (85% $WO_3$) dissolved in water. The total volume of this solution was 7 cc. The impregnation was done in 3 stages, with drying steps between. After impregnation was completed, the catalyst was mixed in a ballmill for 10 minutes, dried in a microwave oven at 25% power for 3 minutes, heat treated at 290° C. for 3 hours, at 425° C. for 3 hours, and finally, at 440° C. for 18 hours.

CATALYST EXAMPLE 2

A catalyst, 1.0 wt % Pd on 100% $Al_2O_3$, was prepared as follows:

SUPPORT: 500.0 g of alumina sol (20% $Al_2O_3$) were evaporated on a hot plate with stirring, dried at 120° C., heat treated at 290° C. for 3 hours and at 425° C. for 3 hours, then ground to 20-35 mesh size.

CATALYST: 5.00 g of the support were impregnated with 4.00 cc of a solution of $PdCl_2$ dissolved in 1N HCl. The solution contained 2.0825 g of $PdCl_2$ per 100 cc, which equals 0.05 g Pd per 4 cc. The $PdCl_2$ solution was added dropwise to the support with constant stirring. It wetted the support completely, but there was no supernatant liquid. The catalyst was mixed in a ballmill for 5 minutes, dried in a microwave oven at 25% power for 3 minutes, then calcined at 290° C. for 3 hours, and finally, at 440° C. for 16 hours.

CATALYST EXAMPLE 3

A catalyst, 1.0 wt % Pd on 90% $Al_2O_3$/10% $SiO_2$, was prepared as follows:

SUPPORT: 450.0 g of alumina sol (20% $Al_2O_3$) and 25.00 g of silica sol (40% $SiO_2$) were mixed together and evaporated on a hot plate with constant stirring, dried at 120° C., heat treated at 290° C. for 3 hours and at 425° C. for 3 hours, then ground to 20-35 mesh size.

CATALYST: 5.00 g of the support were impregnated with 4.00 cc of a solution of $PdCl_2$ dissolved in 1N HCl. The solution contained 2.0825 g of PdCl$_2$ per 100 cc, which equals 0.05 g Pd per 4 cc. The PdCl$_2$ solution was added dropwise to the support with constant stirring. It wetted the support completely, but there was no supernatant liquid. The catalyst was mixed in a ballmill for 5 minutes, dried in a microwave oven at 25% power for 3 minutes, then calcined at 290° C. for 3 hours, and finally, at 440° C. for 16 hours.

CATALYST EXAMPLE 4

A catalyst, 1.0 wt % Pd on 50% Al$_2$O$_3$/50% SiO$_2$, was prepared as follows:

SUPPORT: 750.0 g of alumina sol (20% Al$_2$O$_3$) and 375.0 g of silica sol (40% SiO$_2$) were mixed together. The mixture gelled immediately. It was mixed thoroughly by hand, was dried at 120° C., heat treated at 290° C. for 3 hours and at 425° C. for 3 hours, then ground to 20-35 mesh size.

CATALYST: 5.00 g of the support were impregnated with 4.00 cc of a solution of PdCl$_2$ dissolved in 1N HCl. The solution contained 2.0825 g of PdCl$_2$ per 100 cc, which equals 0.05 g Pd per 4 cc. The PdCl$_2$ solution was added dropwise to the support with constant stirring. It wetted the support completely, but there was no supernatant liquid. The catalyst was mixed in a ballmill for 5 minutes, dried in a microwave oven at 25% power for 3 minutes, then calcined at 290° C. for 3 hours, and finally, at 440° C. for 16 hours.

CATALYST EXAMPLE 5

A catalyst, 1.0 wt % Pd and 0.1 wt % W on 90% Al$_2$O$_3$/10% SiO$_2$, was prepared as follows:

SUPPORT: 450.0 g of alumina sol (20% Al$_2$O$_3$) and 25.00 g of silica sol (40% SiO$_2$) were mixed together and evaporated on a hot plate with constant stirring, dried at 120° C., heat treated at 290° C. for 3 hours and at 425° C. for 3 hours, then ground to 20-35 mesh size.

CATALYST: 5.00 g of the above support were impregnated with a solution consisting of 4.00 cc of a solution of PdCl$_2$ dissolved in 1N HCl, and of 1.00 cc of a solution of ammonium-meta-tungstate (85% WO$_3$) dissolved in water. The PdCl$_2$ solution contained 2.0825 g of PdCl$_2$ per 100 cc, which equals 0.05 g of Pd per 4.00 cc. The ammonium-meta-tungstate solution contained 0.1854 g of AMT per 25 cc, which equals 0.01 g of W per 2.00 cc. The solution was added dropwise to the support with constant stirring. It wetted the support completely, but there was no supernatant liquid. The catalyst was mixed in a ballmill for 5 minutes, dried in a microwave oven at 25% power for 3 minutes, then calcined at 290° C. for 3 hours, and finally, at 440° C. for 16 hours.

CATALYST EXAMPLE 6

A catalyst, 2.0 wt % Pd on 90% Al$_2$O$_3$/10% SiO$_2$, was prepared as follows:

SUPPORT: 1,350.0 g of alumina sol (20% Al$_2$O$_3$) and 75.0 g of silica sol (40% SiO$_2$) were mixed and heated on a hot plate with stirring, dried at 120° C., heat treated at 290° C. for 3 hours and at 425° C. for 3 hours, then ground to 20-35 mesh size.

CATALYST: 5.00 of the support were impregnated with 8.00 cc of a solution containing PdCl$_2$ dissolved in 1N HCl. The solution contained 2.0825 g of PdCl$_2$ per 100.00 cc, which equals 0.10 g of Pd per 8.00 cc. The impregnation was done in several steps, with ballmill mixing and drying steps in between. The final ballmill mixing was 3 minutes and final drying was 3 minutes at 25% power in the microwave oven. The catalyst was heat treated at 290° for 3 hours, and finally, at 440° C. for 16 hours.

CATALYST EXAMPLE 7

A catalyst, 2.0 wt % Pd and 0.2 wt % Cr on 90% Al$_2$O$_3$/10% SiO$_2$, was prepared as follows:

SUPPORT: 1,350.0 g of alumina sol (20% Al$_2$O$_3$) and 75.0 g of silica sol (40% SiO$_2$) were mixed and heated on a hot plate with stirring, dried at 120° C., heat treated at 290° C. for 3 hours and at 425° C. for 3 hours, then ground to 20-35 mesh size.

CATALYST: 5.00 g of the support were impregnated with a solution consisting of 8.00 cc of a solution containing PdCl$_2$ dissolved in 1N HCl, containing 2.0825 g PdCl$_2$ per 100 cc, and 2.00 cc of a solution of Cr(NO$_3$)$_3$ 9H$_2$O in water. This solution contained 0.9620 g of Cr(NO$_3$) 9H$_2$O per 25.00 cc. The impregnation was done in several steps, with ballmill mixing and drying steps in between. The final ballmill mixing was 3 minutes and final drying was 3 minutes at 25% power in the microwave oven. The catalyst was heat treated at 290° C. for 3 hours, and finally, at 440° C. for 16 hours.

CATALYST EXAMPLE 8

A catalyst, 2.0 wt % Pd and 0.2 wt % Ni on 90% Al$_2$O$_3$/10% SiO$_2$, was prepared as follows:

SUPPORT: 1,350.0 g of alumina sol (20% Al$_2$O$_3$) and 75.0 g of silica sol (40% SiO$_2$) were mixed and heated on a hot plate with stirring, dried at 120° C., heat treated at 290° C. for 3 hours and at 425° C. for 3 hours, then ground to 20-35 mesh size.

CATALYST: Procedure the same as for Example 11, but instead of the chromium solution, the following was used: 2.00 cc of a solution of Ni(NO$_3$)$_2$ 6H$_2$O in water. This solution contained 0.6191 g of Ni(NO$_3$)$_2$ 6H$_2$O per 25.00 cc, which equals 0.010 g Ni per 2.00 cc.

CATALYST EXAMPLE 9

A catalyst, 2.0 wt % Pd and 0.2 wt % Co on 90% Al$_2$O$_3$/10% SiO$_2$, was prepared as follows:

SUPPORT: 1,350.0 g of alumina sol (20% Al$_2$O$_3$) and 75.0 g of silica sol (40% SiO$_2$) were mixed and heated on a hot plate with stirring, dried at 120° C., heat treated at 290° C. for 3 hours and at 425° C. for 3 hours, then ground to 20-35 mesh size.

CATALYST: 5.00 g of the support were impregnated with a solution consisting of 8.00 cc of a solution containing PdCl$_2$ dissolved in 1N HCl, containing 2.0825 g PdCl$_2$ per 100 cc, and 2.00 cc of a solution of Co(NO$_3$)$_2$ 6H$_2$O in water. This solution contained 0.6174 g of Co(NO$_3$) 6H$_2$O per 25.00 cc. The impregnation was done in several steps, with ballmill mixing and drying steps in between. The final ballmill mixing was 3 minutes and final drying was 3 minutes at 25% power in the microwave oven. The catalyst was heat treated at 290° C. for 3 hours, and finally, at 440° C. for 16 hours.

The other catalysts shown in Table 1 were made in the manner described for the catalysts of Examples 1-9. Percents are weight percent.

In the following process examples 19-35, summarized in the table, 2-5 mL of the catalyst listed in the second column were packed in a ⅜ inch O. D. Vycor tube followed by 5 mL of 20-35 mesh quartz chips as a preheating zone. The tube was fitted with a gas inlet and rubber septum for the introduction of liquid feed by syringe, then placed in a suitcase furnace heated to 280° C. The gas inlet was connected to a Brooks mass flow controller calibrated for either nitrogen or hydrogen, and the tube exit connected to a trap containing 30 ml of toluene cooled to 0° C. in an ice bath. The exit tube of the trap was connected by a length of heavy rubber tubing to a ⅜ in. s.s. tube which vents the gas feed from the trap. Nitrogen was then fed through the reactor, trap and vent tube at 50–100 mL/min until no air remained in the system. Then hydrogen gas was fed through the reactor for 1 h before 2-methylglutaronitrile was fed by syringe pump into the reactor. After 4 h, the addition of MGN was discontinued and the gas feed switched from hydrogen to nitrogen, product being collected for the last hour for analysis. Nitrogen was flushed through the system until no hydrogen remained in the system, then the trap was removed and 0.16 g of undecane added to the scrubbing solution as g.c. internal standard and the mixture analyzed by gas chromotography/mass spectrometry. The mol ratio of $H_2$ to 2-methylglutaronitrile was 40, and the furnace temperature was 280° C. Contact time was about 2.4 seconds in each run. In the examples the reactor pressure was substantially atmospheric and the MGN was in the vapor phase.

in the light of the foregoing disclosure and discussion without departing from the spirit and scope of the disclosure or from the scope of the claims.

What we claim is:

1. A process for making 3-methylpyridine by contacting 2-methylglutaronitrile in admixture with hydrogen gas with a supported solid catalyst containing palladium metal promoted with at least one of Cr, W, Ni, Co and Ge.

2. A process according to claim 1 wherein the catalyst contains W.

3. A process according to claim 1 wherein the catalyst contains Cr.

4. A process according to claim 1 wherein the catalyst contains Ni.

5. A process according to claim 1 wherein the catalyst contains Co.

6. A process according to claim 1 wherein the catalyst contains Ge.

7. A process of claim 1 wherein the support contains zero to 30 weight percent silica and 100 to 70 weight percent alumina.

TABLE 1

| Example No. | Catalyst Example No. | Catalyst Description | % Conversion of 2-Methyl-glutaronitrile | % Yield 3-Methyl-pyridine |
|---|---|---|---|---|
| 19 | 4 | 1% Pd on 50% $Al_2O_3$/50% $SiO_2$ | 100 | 58.9 |
| 20 | 10 | 1% Pd + 0.1% Cr on 50% $Al_2O_3$/50% $SiO_2$ | 100 | 65.4 |
| 21 | 1 | 1% Pd + 0.1% W on 50% $Al_2O_3$/50% $SiO_2$ | 99.3 | 66.4 |
| 22 | 11 | 1% Pd + 0.1% Ge on 50% $Al_2O_3$/50% $SiO_2$ | 100 | 66.2 |
| 23 | 12 | 1% Pd + 0.1% Co on 50% $Al_2O_3$/50% $SiO_2$ | 100 | 67.2 |
| 24 | 13 | 1% Pd + 0.1% Ni on 50% $Al_2O_3$/50% $SiO_2$ | 100 | 62.1 |
| 25 | 14 | 1% Pd + 0.1% Co + 0.1% W on 50% $Al_2O_3$/50% $SiO_2$ | 100 | 72.1 |
| 26 | 15 | 1% Pd + 0.1% Ni + 0.1% Ge on 50% $Al_2O_3$/50% $SiO_2$ | 100 | 68.7 |
| 19 | 4 | 1% Pd on 50% $Al_2O_3$/50% $SiO_2$ | 100 | 58.9 |
| 21 | 1 | 1% Pd + 0.1% W on 50% $Al_2O_3$/50% $SiO_2$ | 99.3 | 66.4 |
| 27 | 17 | 1% Pd + 0.1% W on 85% $Al_2O_3$/15% $SiO_2$ | 100 | 70.1 |
| 28 | 5 | 1% Pd + 0.1% W on 90% $Al_2O_3$/10% $SiO_2$ | 100 | 78.0 |
| 29 | 18 | 1% Pd + 0.1% W on 100% $Al_2O_3$ | 100 | 77.6 |
| 30 | 3 | 1% Pd on 90% $Al_2O_3$/10% $SiO_2$ | 100 | 68.6 |
| 28 | 5 | 1% Pd + 0.1% W on 90% $Al_2O_3$/10% $SiO_2$ | 100 | 78.0 |
| 31 | 6 | 2% PD on 90% $AL_2O_3$/10% $SiO_2$ | 100 | 69.7 |
| 32 | 7 | 2% Pd + 0.2% Cr on 90% $Al_2O_3$/10% $SiO_2$ | 100 | 77.4 |
| 33 | 9 | 2% Pd + 0.2% Ni on 90% $Al_2O_3$/10% $SiO_2$ | 100 | 78.0 |
| 34 | 9 | 2% Pd + 0.2% Co on 90% $Al_2O_3$/10% $SiO_2$ | 100 | 74.2 |
| 35 | 2 | 1% Pd on 100% $Al_2O_3$ | 100 | 62.1 |
| 29 | 18 | 1% Pd + 0.1% W on 100% $Al_2O_3$ | 100 | 77.6 |

As will be evident to those skilled in the art, various modifications of this invention can be made or followed

* * * * *